(12) United States Patent
Topping et al.

(10) Patent No.: US 6,631,199 B1
(45) Date of Patent: Oct. 7, 2003

(54) AUTOMATED IDENTIFICATION THROUGH ANALYSIS OF OPTICAL BIREFRINGENCE WITHIN NAIL BEDS

(76) Inventors: Allen W. L. Topping, 44 Delmar St., San Francisco, CA (US) 94117; Vladimir Kupershmidt, 3124 Weymonth Ct., Pleasanton, CA (US) 94588; Austin Gormley, P.O. Box 1093, Little River, SC (US) 29566-1093

( * ) Notice: Subject to any disclaimer, the term of this patent is extended or adjusted under 35 U.S.C. 154(b) by 0 days.

(21) Appl. No.: 09/207,339

(22) Filed: Dec. 8, 1998

(51) Int. Cl.[7] .................................................. G06K 9/00
(52) U.S. Cl. ........................ 382/115; 340/5.82; 356/71
(58) Field of Search ................. 382/115–119, 124–126, 382/100; 340/825.31, 825.34, 5.82, 5.52, 5.83, 5.53; 235/380, 382.5, 382; 902/3–6; 713/182–186; 356/485, 512, 618, 71; 359/741

(56) References Cited

U.S. PATENT DOCUMENTS

| | | | | |
|---|---|---|---|---|
| 5,130,852 A | * | 7/1992 | Hamanaka | 359/741 |
| 5,359,669 A | * | 10/1994 | Shanley et al. | 382/117 |
| 5,694,216 A | * | 12/1997 | Riza | 356/485 |
| 5,751,835 A | * | 5/1998 | Topping et al. | 382/115 |
| 5,892,838 A | * | 4/1999 | Brady | 382/115 |

* cited by examiner

*Primary Examiner*—Samir Ahmed
*Assistant Examiner*—Vikkram Bali (57) ABSTRACT

A system for encoding, comparing, and recognizing individuals by analysis of their fingernails employs collimated light having finite bandwidth (810). The light (810) is divided into polarized scanning and reference beams (945) and (846). The scanning beam scans across a subject's nail bed (1010), and the light (1020) reflected from the birefringent component within the nail bed is compared with the reference beam (846). As the scanning beam (945) scans across the subject's nail bed, more or less light reflects from the nail bed (1010), according to the peaks and valleys in the epidermal folds (1000) of the nail bed. The reflected light is analyzed and reduced to binary data as a function of position across the subject's nail bed. These binary data are used to uniquely identify an individual. The data from a scan can be compared with stored data in a pattern recognition algorithm (2000), resulting in a positive or negative identification of an individual.

14 Claims, 9 Drawing Sheets

FIG. 1– PRIOR ART

FIG. 2– PRIOR ART
TOP VIEW

AUTOMATED IDENTIFICATION THROUGH ANALYSIS OF OPTICAL BIREFRINGENCE WITHIN NAIL BEDS

BACKGROUND

1. Field of Invention

This invention relates to human identification technology, particularly to a method and apparatus for producing identifying data unique to a person through examination and characterization of the person's fingernail bed or other distinguishing anatomical part.

2. Prior-Art

Generally Accepted Identification Schemes

Prior-art personnel identification schemes rely on pictorial recognition, voice printing, fingerprinting, DNA matching fingerprinting, and retinal scanning, among others. In general there are many means which measure unique physical properties of the person or environmental tracings created by the person. Each method, however, has one or more drawbacks or disadvantages. DNA matching and fingerprinting is relatively slow and expensive. The other methods are susceptible to errors which arise from changes due to aging, hoarseness, surface injuries, and the like.

3. Prior-Art

U.S. Pat. No. 5,751,835

In our U.S. Pat. No. 5,751,835 (1998), we teach a method and apparatus which uses two distinct wavelengths of light to discern the internal structure of an individual's nail beds. While this system works well, it is more expensive to manufacture than the instant invention.

OBJECTS AND ADVANTAGES

Accordingly, several objects and advantages of the present invention are to provide an improved method and apparatus for rapid identification of individuals which is relatively fast and inexpensive and which is not susceptible to errors which arise from changes due to aging, hoarseness, surface injuries, and the like. Other objects are to provide a means for identifying individuals, which does not carry the social stigma of law enforcement, which does not require the storage or manipulation of vast amounts of data as are used in prior-art schemes, and which is neither cumbersome nor intrusive. Another object is to provide a means for identification of individuals, which is computerized and can yield unambiguous results, and which automatically analyzes fingernail beds. Another object is to provide a system in which the data reduces to a naturally created "barcode". A further object is to provide a system which is insensitive to differences in the angular orientation of the subject's finger, relative to the apparatus. Still another object is to identify individuals through analysis of the birefringent material in their nail beds.

Additional objects and advantages will become apparent from a consideration of the drawings and ensuing description thereof

SUMMARY

In accordance with the present invention, a method and apparatus are provided which uses broadband optical interferometry to selectively illuminate successive discrete portions of an individual, such as fingernails, detect reflected light from this illumination with photodetectors, analyze this detected light, and present results indicative of the identity of the individual.

Figure 1:
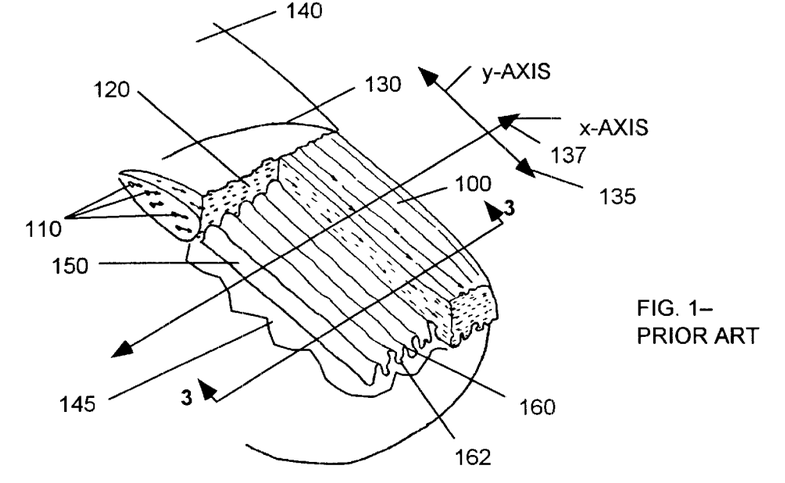
FIG. 1 is a cut-away view of a fingernail or toenail.
Figure 2:
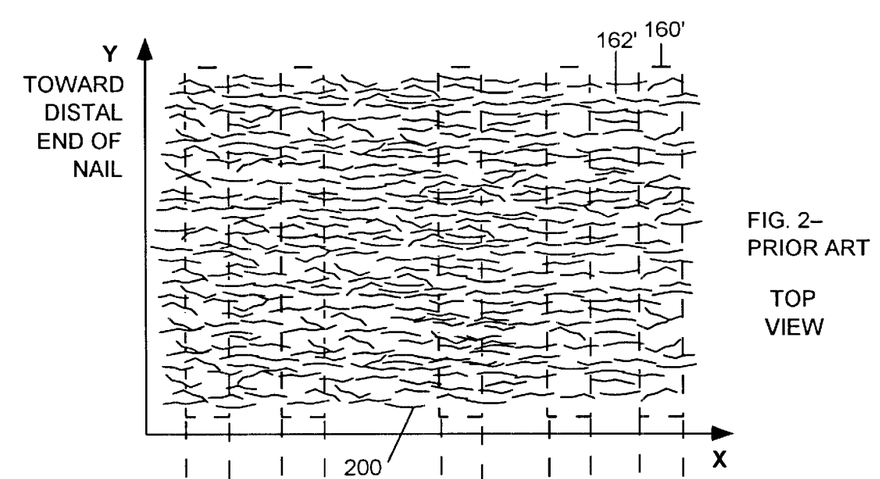
FIG. 2 is a top view of the interior structure of a nail.
Figure 3:
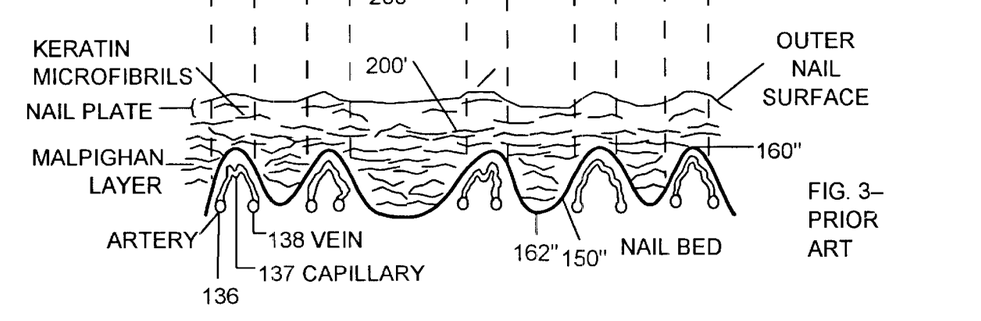
FIG. 3 is a cross-sectional view of the interior structure of a nail taken at line 3—3 of FIG. 1.

Physical Structure and Dermal Topography of Nail Bed—FIGS. 1–3

As shown in FIG. 1, a human fingernail 100, at the terminus of finger 140, results from the continued regeneration of specialized cells 110 that are pushed out from a growth plate 120 in the direction of y-axis 135. In the present discussion, fingernail 100 is also referred to as a "nail plate". Growth plate 120 lies beneath cuticle 130, at the base of nail 100. Cells 110 comprise primarily the protein keratin, which in nail 100 comprises a hard, flattened, translucent, horny material. As more cells 110 emerge from growth plate 120, fingernail 100 grows and migrates away from cuticle 130 toward the terminus of finger 140. Fingernail 100 grows on top of a nail bed 150. Nail bed 150 rests on a lower, fleshy surface 145. Nail bed 150 is a grooved structure comprising nearly parallel and irregularly separated columns of toughened, blood-perfused flesh extending parallel to y-axis 135. Blood to nourish bed 150 is carried by arteries 136 (FIG. 3) to capillaries 137, and then back by veins 138.

The width, height, and distance between the parallel columns comprising arches 160 and valleys 162 of bed 150 vary with the age and the size of the individual. The width of these columns varies from 0.13 to 0.25 mm (0.005 to 0.01 inch). The spacings from groove to groove remain proportionally constant over the entire life of the individual, in similar fashion to the loops and whorls of a fingerprint. Thus, unlike facial characteristics, these spacings can be used to identify and distinguish an individual over his or her entire lifetime.

As nail 100 grows, keratin is laid down in the form of microfibrils 200, as depicted in FIGS. 2 and 3. A microfibril is a small, thread-like fiber or filament which is a constituent of a larger structure, in the present case nail 100. The majority of microfibrils 200 within the nail bed are aligned parallel to the x-axis (FIG. 1). The maximum density of microfibrils 200 is located at the interface of the nail bed and the nail plate.

FIG. 2 is a magnified, top view of nail plate 100. FIG. 3 is a cross-sectional view of nail 100 and bed 150 (3—3 in FIG. 1). FIG. 3 is magnified the same amount as FIG. 2 and the two drawings are aligned along the x-axis. Five individual, parallel columns comprising arches 160 (FIG. 1) are indicated. Dashed lines connect the position of these columns in the two views of FIGS. 2 and 3.

The dermal structure associated with the nail bed is called the Malpighian layer. Because of their size, optical translucency, and orientation, the microfibrils cause the Malpighian layer to be optically birefringent. A birefringent material resolves a light wave into two unequally reflected waves. These waves are generally polarized in directions which are mutually orthogonal. Thus light which is reflected from the Malpighian layer can be analyzed by a system which is sensitive to polarized light.

Figure 4:
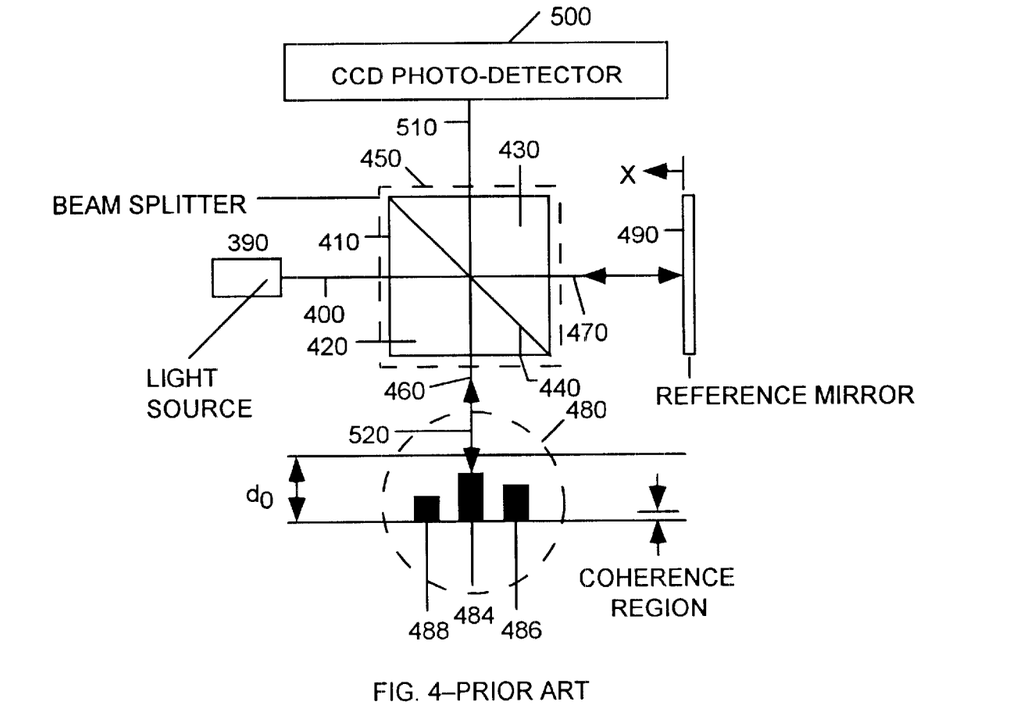
FIG. 4 is a schematic drawing showing the main elements of a prior-art interferometer.
Figure 5:
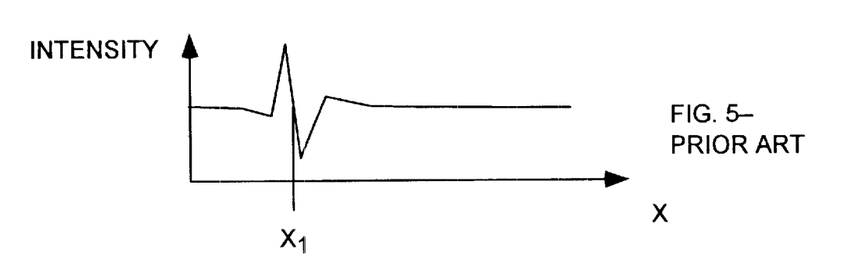
FIG. 5 is a plot of intensity vs. distance in the diagram of FIG. 4.
Figure 6:
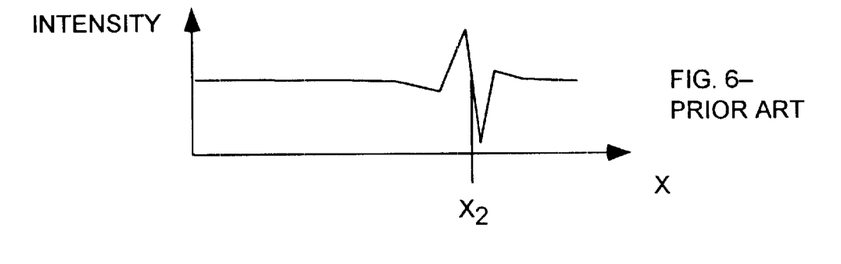
FIG. 6 is a plot of intensity vs. distance in the diagram of FIG. 4.

Broadband Optical Interferometry—FIGS. 4–6

A broadband prior-art interferometer system is shown diagrammatically in FIG. 4. This system will be discussed prior to discussing the present system in order to explain the principles involved. A beam 400 of light from a broadband source 390, e.g., an incandescent source, is directed at a beam splitter 450. Such a beam splitter, well known to those in the field of optics, generally comprises a pair of isosceles prisms 420 and 430. The prisms are joined and form an interface 440 at their hypotenuse surfaces. In this particular example, beam splitter 450 is of a type designed to minimize the polarization of transmitted and reflected light.

Incident beam 400 passes through the first surface 410 of prism 420 and continues to interface 440. At this interface, beam 400 splits into two components 460 and 470 which typically have equal amplitudes. Component 460 is deflected downward toward an object (484, 486, or 488) among objects 480 to be examined. Component 470 passes undeflected toward movable reference mirror 490.

Component 460 is reflected from object 484, for example, and passes upward through interface 440, finally terminating on photodetector 500. As component 460 passes through interface 440, half of its energy is directed back into source beam 400 and is lost. The other half impinges on detector 500.

Component 470 is reflected from mirror 490 and re-enters beam splitter 450. At interface 440, half of the energy in beam 470 is deflected upward toward detector 500. The other half of the energy in beam 470 continues through interface 440, through prism 420, and out front surface 410 of beam splitter 450, where it is lost. (Some energy is lost at the mirrors and in the splitter, but this will be ignored to simplify the explanation.)

Components 460 and 470 share a common path 510 from interface 440 in beam splitter 450. Path 510 originates at interface 440 and terminates at the surface of detector 500.

Light beam 400 is an electromagnetic wave. It comprises both an electrical and a magnetic component. These components are oriented and measured perpendicular to beam 400 and constitute the "wavefront" of beam 400. Because of this orthogonal orientation, beam 400 is also called a "transverse" beam. The amplitudes of the electrical and magnetic components of beam 400 vary sinusoidally as they propagate along beam 400. The two sinusoidal components are separated in phase by an angle of 90 degrees, i.e., the amplitude of the magnetic component is zero when the amplitude of the electric component is at a maximum, and so forth. The mathematical descriptions of the two components are equivalent. Because of their fixed and equivalent relationship, it is normally sufficient to perform calculations on just one of the components. The electrical component, E, is typically chosen. E is a vector quantity, represented in boldface type. (The magnetic vector is normally represented by the symbol M.)

If beam 400 were monochromatic, e.g. if it came from a laser, it would propagate through space as a pure sine wave of single frequency. At any point along the length of beam 400, its electrical and magnetic vectors are exactly 90 degrees out of phase. Such a wave is said to be "coherent." Imagine that beam 400 and a second, identical beam impinge at the same location on a surface, forming a spot of light. The two beams of light are said to interfere. If the two beams were exactly in phase, the amplitude E (plain-face type) of their summed E vectors is equal to 2E. The spot would be twice as bright as that caused by either beam alone. This is called "constructive" interference since they are in phase and their spots add. If the two beams were exactly out of phase, their vectors would cancel and the amplitude E of their summed E vectors would be zero and the spot would be absent. This is called "destructive" interference. Because the beams are monochromatic, this interference phenomenon can be observed at a point anywhere along their extent. (This is true provided they coincide; not if they come from separate sources.) The coherence region is thus very long. The study of interfering light beams is called interferometry.

In the case of white light, i.e., very broad-spectrum light comprising all visible wavelengths, all phases and wavelengths are present and the light is said to be "incoherent". In this case, the coherence region is infinitesimally short.

In intermediate cases, it is desirable to use light containing more than a single wavelength, but limited in bandwidth. Multiple-wavelength beams can still be said to interfere, although this interference is observed only over relatively short distances, i.e., the coherence region is relatively short, but not zero.

The length of the coherence region is determined by the spectral bandwidth of beam 400. The greater the bandwidth, the shorter the coherence length. In a typical application light with a central wavelength of 640 nm and a spectral bandwidth of 40 nm has a coherence length of approximately 5 $\mu$m. This light is no longer considered "monochromatic" since it contains more than a single wavelength. It is generally specified in terms of a central wavelength and a bandwidth around the central value.

If beam 460 impinges on the top of object 484 and the path lengths of beams 460 and 470 are equal, interference between the two beams will occur at the surface of photodetector 500. If object assembly 480 is moved to the right, such that beam 460 is reflected from more distant object 488, interference will not occur. This is because the path length difference between beams 460 and 470 is greater than the coherence length of the light in beam 400.

If the position of reference mirror 490 is changed such that path lengths 460 and 470 are equal when beam 460 is reflected from the top of object 488, then interference will occur for object 488, but not for objects 484 and 486. By moving mirror 490 in the "X" direction and also moving object collection 480 in a predetermined fashion, it is possible to completely map the positions and depths of objects 484, 486, and 488 within collection 480.

Beams 460 and the upwardly reflected component of 470 are both directed at the same location on the surface of photodetector 500. Detector 500 can be a Charge-Coupled-Device (CCD), or a photodiode, or the like. The amplitude or intensity of light impinging on the surface of detector 500 is equal to the magnitude of the sum of the vector intensities of beams 460 and 470. In the case of a CCD, an image of the objects within collection 480 can be formed, as described below.

When interference is absent, photodetector 500 will register an amount of incident light equal to the intensity of beam 400, minus absorption and reflection losses. In this case, beams 460 and 470 add as though they are incoherent.

When interference is present, photodetector 500 will register slightly greater and slightly smaller amplitudes around the above central value. This amplitude variation is due to the constructive and destructive interference of the light reflected from mirror 490 and objects within collection 480.

For example, assume beam 460 impinges on the top of object 484 and mirror 490 is moved in the "X" direction. When the path lengths of beams 460 and 470 are equal, interference will occur. Two plots of intensity detected by detector 500 vs. position of the reference mirror are shown in FIGS. 5 and 6. In FIG. 5, interference is indicated when beam 460 impinges on the top surface of object 484 and mirror 490 is at $X_1$. In FIG. 6, interference occurs when beam 460 impinges on the top surface of object 486 and mirror 490 is at $X_2$. The difference in height of objects 484 and 486 is simply $X_2$ minus $X_1$. The mathematical description of the shape of the intensity variations during interference is discussed below.

It is possible to provide an image of objects 484, 486, and 488 contained in collection 480. Beam 460 can be scanned across the top of these objects, or collection 480 can be moved so that beam 460 is reflected from all surfaces in collection 480. An electromechanical connection (not shown) can be made to an X-Y oscillograph (not shown) in which the oscillograph spot moves with the position of beam 460 in pantographic, i.e. synchronized, fashion. While this scan is in progress, reference mirror 490 is moved back and forth in the X direction a distance equal to or slightly greater than $d_o$ (FIG. 4). The output of detector 500 is connected to the brightness input of the X-Y oscillograph. Interferences are then imaged as brighter spots, in well-known fashion.

Great precision must be maintained in the design and manufacture of beam splitter 450, the positioning of object collection 480, reference mirror 490, and detector 500 relative to beam splitter 450, the alignment of incident beam 400, and the like. These requirements are well understood by those familiar with interferometry.

Figure 7:
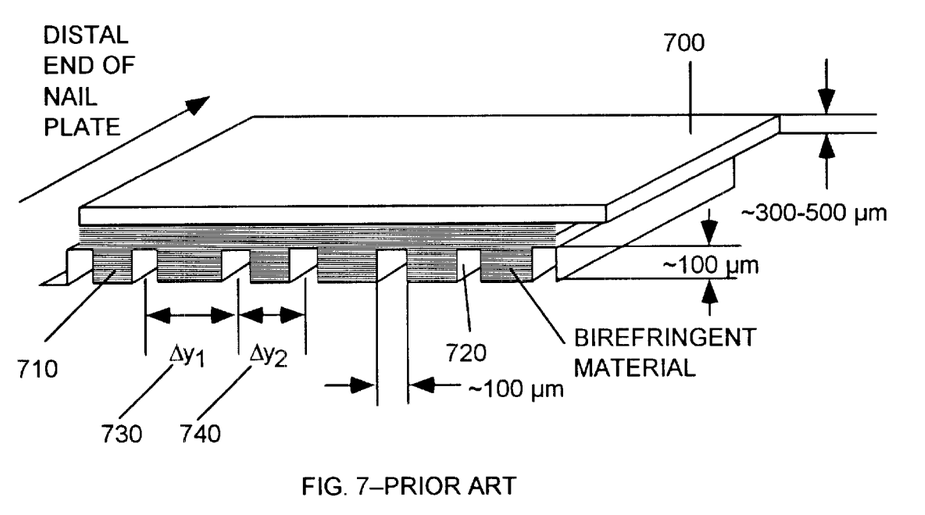
FIG. 7 is a model of a fingernail or toenail.

Model of a Fingernail or Toenail—FIG. 7

The critical elements examined by the present identification system are the nail, the Malpighian layer, and the relative spacing between the longitudinal ridges beneath the surface of the nail plate. FIG. 7 shows a schematic diagram of these elements. The outer layer 700, of thickness between 300 and 500 $\mu$m, is less rich in keratin microfibrils. Beneath layer 700 is layer 710, the Malpighian layer, which is rich in keratin microfibrils. Layer 710 surrounds ridges 720 (160 in FIG. 1). Unequal distances 730 and 740 are unique to each individual. The relative spacings of ridges 720 are invariant throughout an individual's life. According to the invention, as explained below, these spacings can be used to generate a unique, one-dimensional map of the nail bed. This map is much like a barcode which is contained within the nail. From this map we derive a unique numerical string representing the individual's identity.

Nail bed Scanning System—Preferred Embodiment—FIGS. 8, 9, 10, and 11

Figure 8:
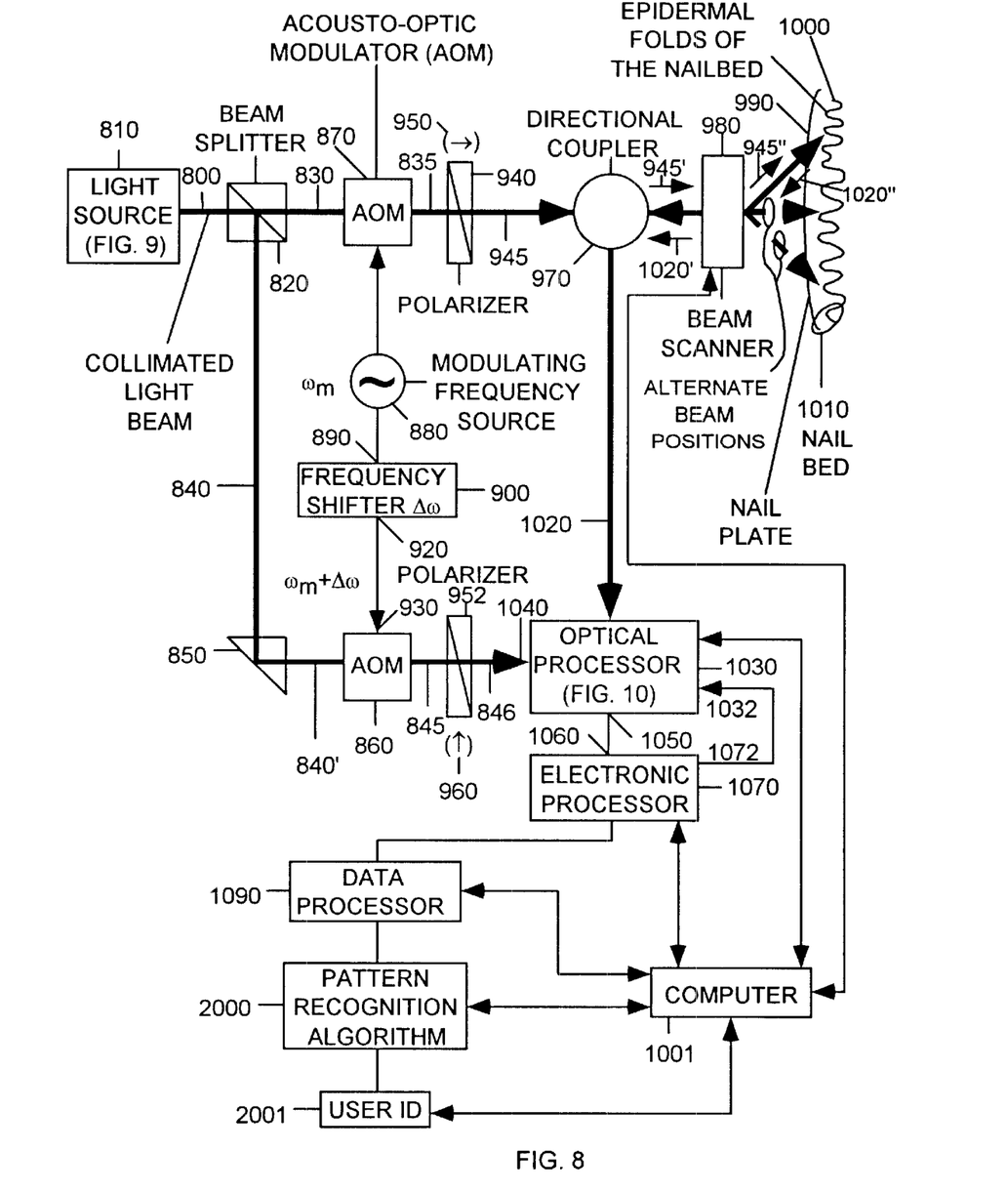
FIG. 8 shows a preferred embodiment of the scanning system according to the present invention.

The interferometric scanning system in FIG. 8 is used to discern the spacings between epidermal folds 1000 (720 in FIG. 7 and 160 in FIG. 1). A multi-wavelength, collimated beam 800 of light from source 810 enters beam splitter 820, as described above in connection with FIG. 4. One embodiment of source 810 is described below in connection with FIG. 9.

Beam 800 is split by splitter 820 into two beams, 830 and 840. A mirror or prism 850 deflects beam 840 into an acousto-optic modulator (AOM) 860. Modulator 860 may be of the Bragg cell type. In response to an externally applied voltage, Bragg cell modulators modulate the intensity of light as it passes through them. They are well known to those familiar with the field of optics and their principles of operation will not be discussed in detail here. Beam 830 enters a second AOM 870. An alternating-current voltage source 880 is connected to AOM 870. The modulating frequency at the output of source 880 is equal to $\omega_m$, typically $2\pi \times 10^6$ radians/sec. Source 880 is also connected to input 890 of frequency shifter circuit 900. Frequency shifter 900 shifts the input frequency $\omega_m$ upward (or downward, if desired) by an amount $\Delta\omega$, typically $2\pi \times 10^3$ radians/sec, in well-known fashion. The output 920 of shifter 900 contains the sum (or difference, if desired) of the two applied frequencies, $\omega_m + \Delta\omega$. This sum of frequencies is applied to input 930 of AOM 860 to modulate beam 845 at this summed rate.

As it leaves AOM 870, beam 835 enters polarizer 940. Polarizer 940 preferably is a prism assembly. Polarizers are well known to those familiar with the art of optics. As it leaves polarizer 940, beam 945 is preferentially linearly polarized in a first direction, as noted by directional arrow 950.

Similarly, beam 845 passes through a second polarizer 952. Polarizer 952 polarizes beam 845 in a second, respectively orthogonal direction, as indicated by directional arrow 960. Polarizers 940 and 952 are said to be "crossed", i.e. their polarization directions are separated by 90 degrees, relative to one-another.

Polarized beam 945 enters a directional coupler 970. Directional couplers are also well known to those familiar with the art of optics. Beam 945 passes through coupler 970 and enters beam scanner 980. As it enters scanner 980, beam 945 is identified as beam 945' in order to show its direction of travel. Beam scanner 980 is preferably a two-dimensional, mirror-galvanometer scanner, well known in the art of optics. Scanner 980 contains two, orthogonally disposed mirror-galvanometers, which are controlled by computer 1001. Scanner 980 is arranged to deflect beam 945' in raster-scan fashion over a two-dimensional region of nail bed 1000.

Beam 945", the continuation of beam 945', penetrates plate 990 and is scattered by (reflected from) the Malpighian layer region between plate 990 and epidermal folds 1000 within nail bed 1010. Reflected beam 1020", which is collinear with beam 945", enters scanner head 980 and is deflected into directional coupler 970. Directional coupler 970 redirects beam 1020 into optical processor 1030.

Beams 1020 and 846 are arranged to impinge at the same location on processor 1030 and their energies are thereby summed. Processor 1030 preferably comprises a reference interferometer and photodetector. Its construction is discussed further in connection with FIG. 10. The summed beams 1020 and 846, which are vector quantities, are converted to a complex output voltage at output 1050 of processor 1030.

Optical processor output 1050 is connected to the input 1060 of electronic processor 1070. Processor 1070 detects the amplitude of the shifting frequency Δω as described below.

Electronic processor 1070 is connected to data processor 1090. Processor 1090 correlates the information obtained from electronic processor 1070 with the x-y positioning of scanner head 980 to provide a series of electronic signals representative of the positions of the epidermal folds within nail bed 1010. This information is unique to each individual.

The epidermal fold positional information is passed from data processor 1090 to a pattern recognition algorithm (described below) which finally provides the identification of the subject whose nail has been scanned.

Figure 13:
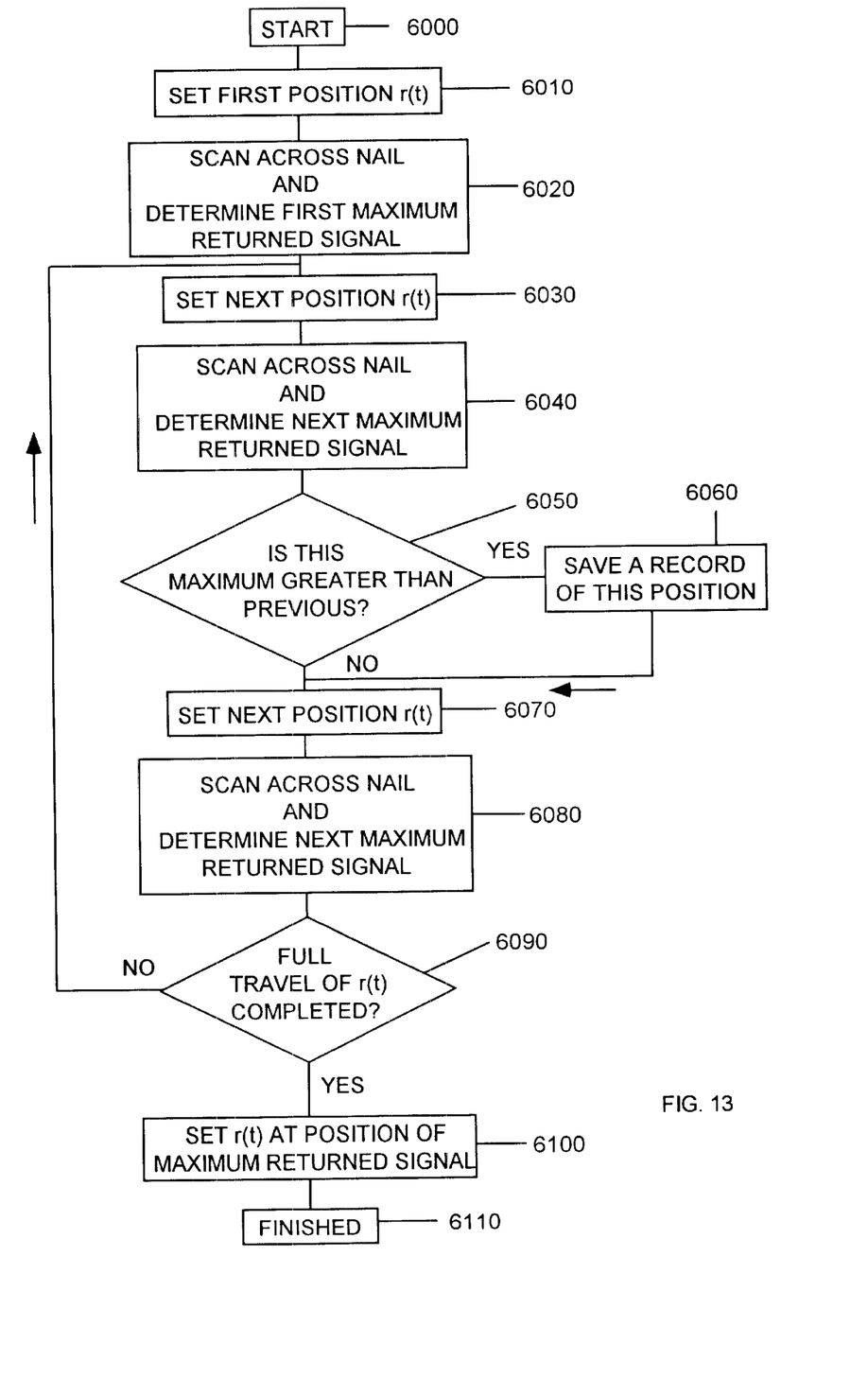
FIG. 13 is a flow diagram which shows optimizing of a scanner output of the system of FIG. 8.
Figure 14:
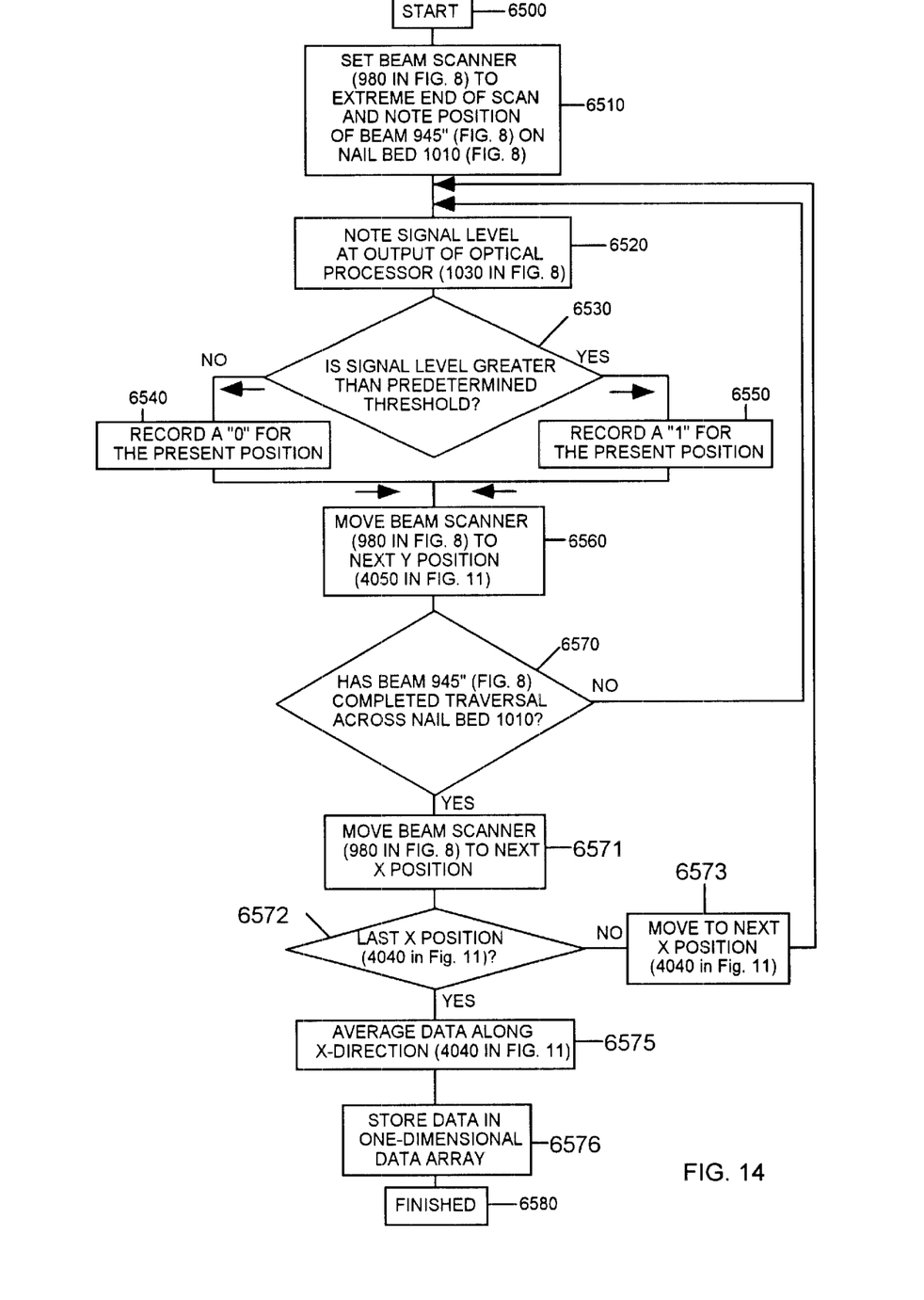
FIG. 14 is a flow diagram showing the operation of a data processor used in the system of FIG. 8.
Figure 15:
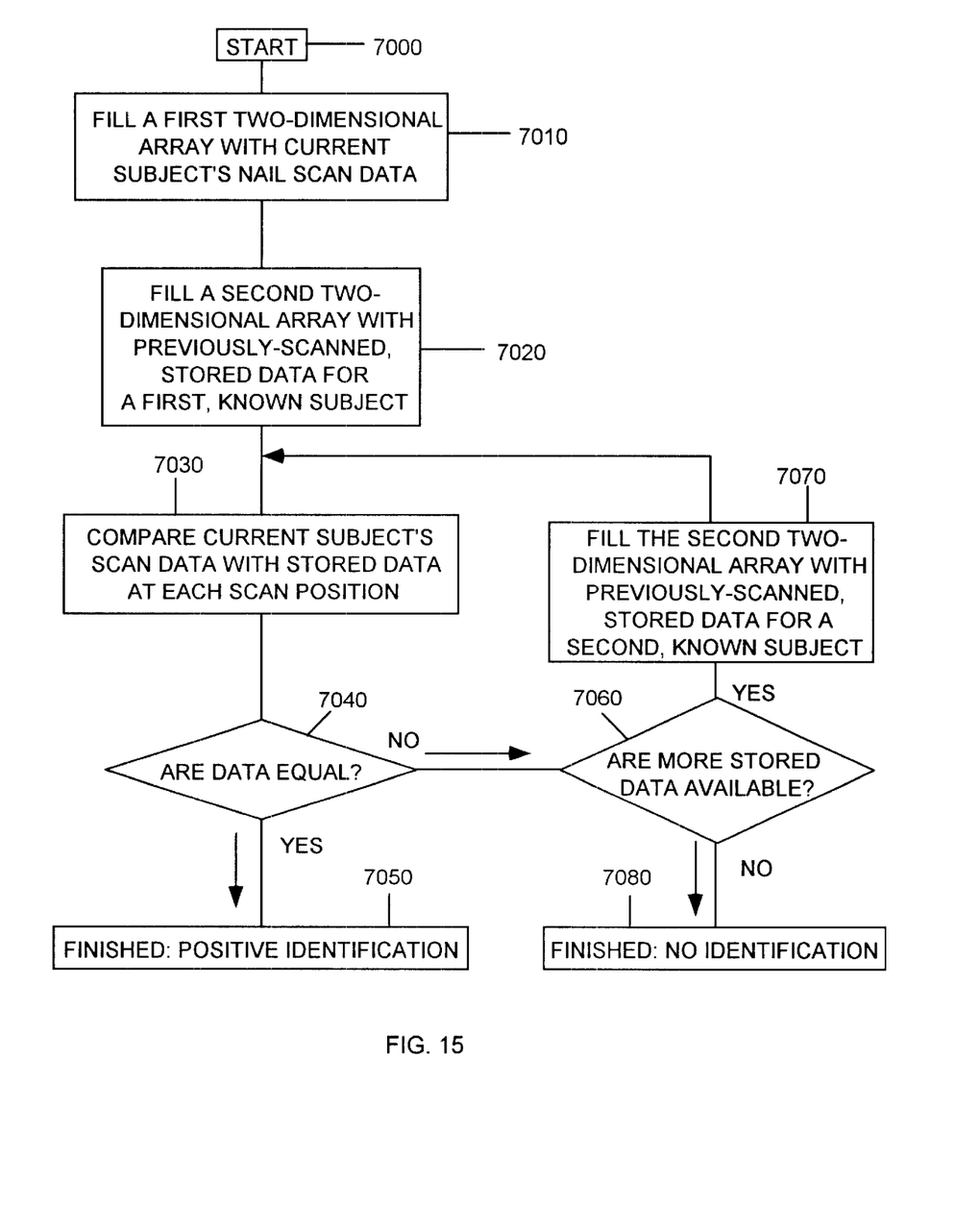
FIG. 15 is a flow diagram showing the operation of a pattern recognition algorithm used in the system of FIG. 8.

Beam scanner 980, optical processor 1030, electronic processor 1070, and data processor 1090, are under the control of computer 1001. Pattern recognition algorithm 2000 is contained in the memory of computer 1001 whose control program is illustrated by the flowcharts of FIGS. 13–15. User ID 2001 is presented through a readout device, such as a monitor (not shown) which is a component of computer 1001.

Figure 9:
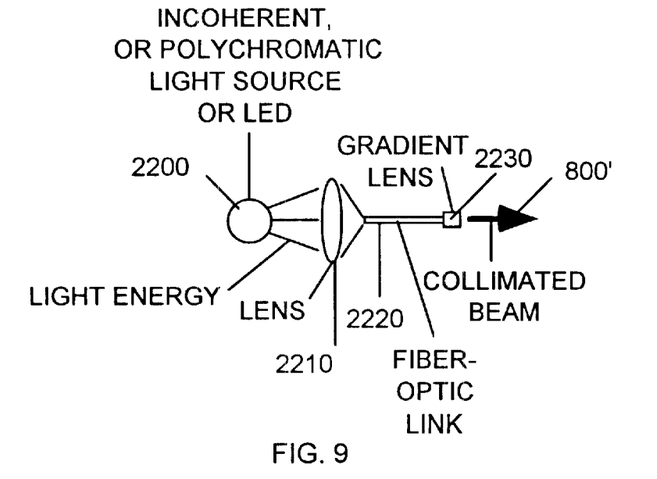
FIG. 9 is a detail drawing showing a light source used in the system of FIG. 8.

Incoherent Light Source—FIG. 9

The output from an incoherent, or polychromatic, light source such as ligh-temitting diode (LED), or bandpass-filtered incandescent lamp 2200, is directed toward lens 2210. Source 2200 preferably emits light at a central wavelength of 640 nanometers (nominally red), with a bandwidth typically between 40 and 60 nanometers. Lens 2210 focuses the light energy on the end of fiberoptic link 2220. A graded-index, collimating lens 2230, well known in the field of fiberoptics, is affixed to the end of fiber 2220. Collimated light beam 800' emerges from lens 2230 and is used in the apparatus of FIG. 8.

Figure 10:
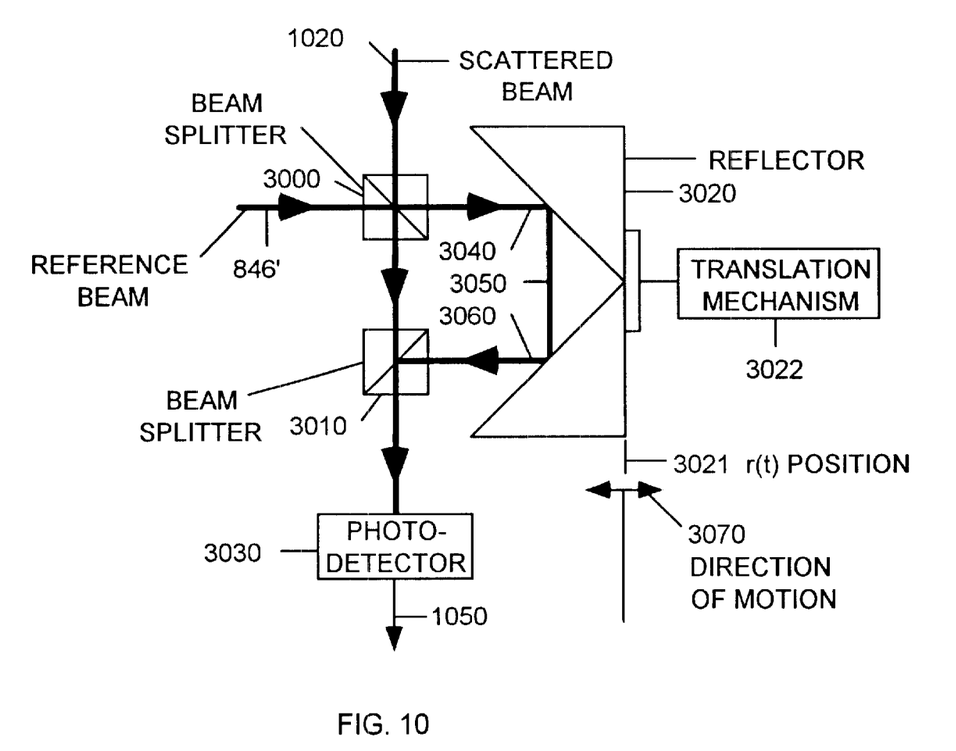
FIG. 10 is a detail drawing showing the elements of an optical processor used in the system of FIG. 8.

Optical Processor—FIG. 10

It was explained in connection with FIG. 4 that the reference and signal path lengths must be equal in order for interference between the two beams to occur. It was further explained in the same connection that portions of the beams are lost for various reasons. The description of the lost components of the beams will not be repeated here.

Optical processor 1030 (FIG. 8) comprises an assembly which equalizes the path lengths of beams 830+835+945+1020 (FIG. 8) and 840+840'+845+846 (FIG. 8). Processor 1030 (FIG. 8) also contains a photodetector with an output 1050 (FIG. 8).

Beam 1020 (FIG. 8), scattered from the region between nail plate 990 (FIG. 8) and folds 1000 (FIG. 8), is directed at a first port of a first beam splitter 3000 (FIG. 10). Beam 1020 (FIG. 8) is split by splitter 3000 and a portion, typically half, passes through splitter 3000 and also through a second beam splitter 3010.

Reference beam 846' enters first beam splitter 3000 (FIG. 10) at an angle which is orthogonal to that of beam 1020. Beam 846' passes through splitter 3000, emerging as beam 3040, which is reflected from reflector 3020 as beam 3050, which is then reflected from reflector 3020 as beam 3060. Beam 3060 is deflected downward by splitter 3010, merging with beam 1020.

The above-described components of beams 1020 and 846' finally impinge on photodetector 3030 where their energies, which are vector quantities, are summed. Only the components with path lengths which differ by less than the coherence length (described above) are important in this present measurement. Those components with path length differences greater than the coherence length contribute a steady-state term which is neglected in the mathematical analysis below.

The mechanical assembly which contains beam splitter 820, modulators 860 and 870, polarizers 940 and 952, directional coupler 970, and optical processor 1030 (all FIG. 8) is normally made to reasonable engineering standards. However, mechanical tolerances, temperature variations, and other factors make it difficult to ensure that the signal and reference paths are exactly equal. In practice the path length of one of the beams, 846', is made adjustable by the addition of a precision translation mechanism 3022, which causes reflector 3020 to move in the directions shown by arrows 3070. Mechanism 3022 is under the control of computer 1001 (FIG. 8). As reflector 3020 moves, the path length of reference beam 846' changes, while that of signal beam 1020 remains constant. (Since only path length is important in this adjustment, beams 1020 and 846' can be interchanged, with the same result.) Proper path length adjustment results in the maximum observable effect when light is scattered (reflected from) the birefringent material contained in nail bed 1010.

Figure 11:
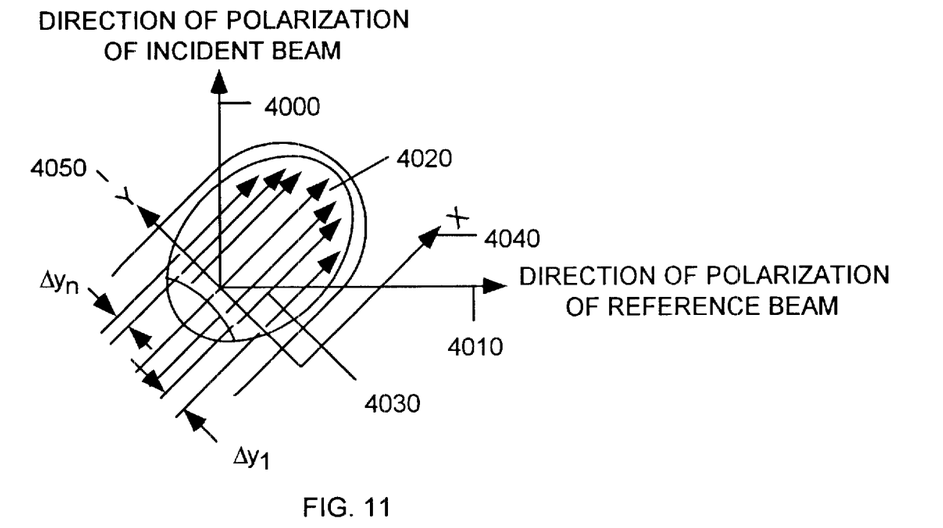
FIG. 11 shows coordinate systems of the nail and the measuring system of FIG. 8.

Coordinate Systems of the Nail and the Measuring System—FIG. 11

The polarization orientations of the incident and reference beams are orthogonal and are identified in FIG. 11 as directions 4000 and 4010, respectively. The x- and y-directions relative to the orientation of epidermal folds 4030 of nail 4020 are identified as directions 4040 and 4050, respectively.

Measurement Conditions—FIGS. 8, 10

The bandwidth of light source 810 (FIG. 8) is chosen such that the coherence length within nail bed 1010 is between 5 and 10 $\mu$m. The incident electric field amplitude of beam 945 is:

$$E_o = e_o E_o(t) \exp\{i(\omega_o + \omega_m)t\}.$$

The amplitude of scattered beam 1020 is:

$$E_{sc} = e_{sc} E_{sc_0}(t - \tau_{sc}) \exp\{i(\omega_o + \omega_m)t + i\delta_{sc}\},$$

where $E_o(t)$ and $E_{sc_0}(t - \tau_{sc})$ are the amplitudes of the incident and scattered waves, 945" and 1020", respectively. $\tau_{sc}$ is the propagation delay of the scattered signal. $\delta_{sc}$ is the phase of the scattered signal 1020". t is time, and i is the square root of minus one.

The amplitude of the electrical component of the reference beam 846 presented to input 1040 of optical processor 1030 is given by:

$$E_r = e_r E_{r_0}(t - \tau_r) \exp\{i(\omega_o + \omega_m + \Delta_{107}) + i\delta_r\}.$$

The total intensity at the input of photodetector 3030 (FIG. 10) is given by:

$$I = |E_r + E_{sc}|^2 = I + (e_r \cdot e_{sc}) \gamma(t) \cos\{(2\pi/\lambda)(\Delta sc + r(t)) + \Delta \omega t\}.$$

$\gamma(t)$ is the coherence or visibility function, well known to those skilled in the art of optics. The visibility function is proportional to the coherence length; when the coherence length is zero, the visibility function equals zero. When the coherence length is infinite, the visibility function equals one.

The product $e_r \cdot e_{sc}$ is the scalar result of multiplication of the intensities of the reference and scattered beams 1020 and 1040 times the cosine of the angle between their two polarization directions. The product $e_r \cdot e_{sc}$ must be approximately 1. This is ensured by proper relative orientation of polarizers 940 and 952 (FIG. 8), and the orientation of nail bed 1010 with respect to beam 945'.

$\Delta\omega$ is the beat frequency between the measurement signal 1020 and the reference signal 1040 presented to optical processor 1030 and is present at the output of processor 1030.

Because of the high birefringency of the nail bed, the direction of polarization of the backscattered (reflected) signal is determined by the nail bed. The principal axis of birefringent keratin layers is oriented perpendicular to the direction of the nail bed ridges. The reference direction of polarization must be adjusted to achieve a maximum signal. This occurs when the reference direction of polarization is parallel to the alignment direction of the keratin microfibrils in nail bed 1010.

$\Delta sc(x,y)$ is a phase shift term due to birefringence which, in turn, is a function of the periodic structure within the nail bed (4030 in FIG. 11). $r(t) = r_0 + \delta r(t)$ is a phase shift term which represents the path length within the reference interferometer of FIG. 10. It is related directly to the position 3021 of reflector 3020 (FIG. 10). The constant offset $r_0$ must be adjusted to the required depth beneath nail plate 990 (FIG. 8). The optimum position of $r_0 = r_{optimum}$ occurs when the scalar value $e_{sc \cdot er}$ is at a maximum. This occurs when $r_{optimum}$ equalizes the path lengths of beams 830 et seq and 840 et seq (FIG. 8) in the maximum-density region of the birefringent layer in nail bed 1010. The variations in path length caused by movement of reflector 3020 (FIG. 10) cause relative variations in the time of arrival of waves 1020 and 846' at the input of photodetector 3030. Thus optical processor 1030 may be considered a variable delay line.

The output of optical processor 1030 (FIG. 8) is the modulation frequency carrier, $\omega_m$, which is amplitude modulated at frequency $\Delta\omega$, and a DC term, which is removed by electronic processor 1070. The amplitude of the modulation is proportional to the visibility function $\gamma(t)$ and the amount of light scattered from the birefringent layer beneath nail plate 990.

In the presence of a birefringence signal, the amplitude of the demodulated output of processor 1030 will increase and then decrease as the path length difference between beams 1020 and 846' varies. The signal reaches a maximum when the overall paths (830 et seq and 840 et seq) are exactly equal.

In the preferred embodiment, beam scanner 980 is oriented so that beams 945" and 1020", which are collinear, scan in raster-scan fashion across nail bed 4020 (FIG. 11). Scanning is done in the "x" and "y" directions 4040 and 4050, respectively. Scans taken in the "y" direction provide a maximum of information from the subject's nail bed. They must be repeated at different "x" locations and the results averaged along the "x" direction. This is done to average out small positional differences or meanderings of folds 1000 (FIG. 8) within the x-y plane of the nail bed structure.

Operation of the Preferred Embodiment— FIGS. 8, 11

Polarizers 940 and 952 (FIG. 8) are oriented so that the polarization direction of beams 846 and 945 are orthogonal. With light source 810 ON, beam scanner 980 scans beam 945" in the "y" direction (4050 in FIG. 11) over nail bed 1010. Electronic processor 1070 (FIG. 8) monitors the amplitude of signal I above. Output 1072 of electronic processor 1070 transmits a signal to input 1032 of optical processor 1030. The signal applied to input 1032 causes reflector 3020 (FIG. 10) to move back or forth as indicated by arrows 3070. This motion continues until the signal at input 1060 of electronic processor 1070 is maximized. With this signal maximized, the system is now ready to take data which will reveal the spacings of the epidermal folds 1000 of nail bed 1010.

After optimization, the output of electronic processor is proportional to $\Delta sc(x,y)$. This is the desired result. At a particular x-location (4040 in FIG. 11), a y scan yields a signal with maxima and minima which correspond to the peaks and valleys of the epidermal folds 1000 (FIG. 8) in nail bed 1010.

This information is refined in data processor 1090. At each y location, data processor 1090 determines whether the output signal of processor 1070 is interpreted as a binary ONE or ZERO. This can be done by thresholding the output of processor 1070, for example. The data available at the output of processor 1090 are ($y_1$, binary value$_1$), ($y_2$, binary value$_2$), and so forth as collinear beams 945" and 1020" are scanned across folds 4030 (FIG. 11).

This information is subsequently fed to a pattern recognition algorithm 2000. This algorithm compares the new data about a queried nail to previously recorded data. When the two data sets match, within a predetermined error rate, an individual is identified. The identification is accomplished by algorithm 2000 which operates within the memory of computer 1001. The computer displays user ID 2001 on a computer monitor screen (not shown) which is connected to computer 1001. If there is no match, the individual's identity has not previously been stored for use by algorithm 2000. At this point the present individual's data can be either stored or discarded.

Figure 12:
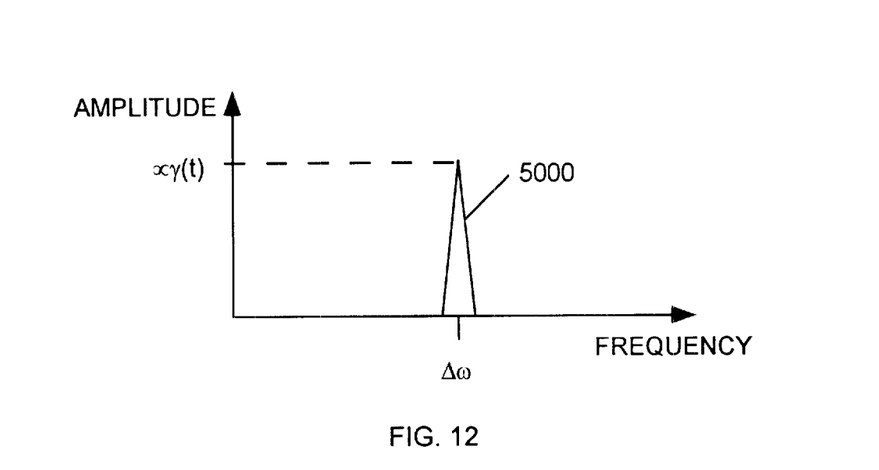
FIG. 12 is a spectrum analysis plot showing $\gamma(t)$ vs. frequency at the output of an electronic processor of FIG. 8.

Spectrum Analyzer Output—FIG. 12

A spectrum analyzer, well known to those in the fields of optics and electronics, can be used to display the output of electronic processor 1070. This output appears as shown in FIG. 12. A signal 5000 with amplitude proportional to the amplitude of the visibility function, $\gamma(t)$, and the light scattered from the birefringent layer beneath nail plate 990 (FIG. 8) will be centered at $\Delta\omega$.

Optimizing the Scanner Output—Flow Diagram— FIG. 13

The scanner output is optimized according to the flow diagram of FIG. 13. First, the scanning system is instructed, preferably by computer 1010 (FIG. 8), to start (6000) taking data. These data comprise a series of calibration functions which optimize the scanner output. Reflector 3020 (FIG. 10) is moved by mechanism 3022 to one extreme end of its travel (6010), corresponding to a first value for $r_1(t)$. A first scan (6020) is made across nail bed 1010 (FIG. 8) and the maximum return signal is noted at the output of electronic processor 1070. Reflector 3020 (FIG. 10) is moved to a next position (6030), $r_2(t)$, typically 0.1 mm to the right or left of the starting position, and another scan (6040) is made across nail bed 1010 (FIG. 8). The maximum return signal from this second scan is compared with that from the previous scan (6050). If the current scan maximum value is greater than that obtained on the previous scan, a record of this position is saved (6060). Reflector 3020 (FIG. 10) is moved to the next position, $r_3(t)$ (6070). Another scan is taken (6080) and the maximum signal from this scan is compared with that of the previous maximum. This process is repeated until the full travel, r(t), available to reflector 3020 has been traversed (6090). At the end of this process, reflector 3020 is moved to the position $r_{optimum}$ which gave the maximum returned signal (6100). At this point, the signal and reference path lengths (830 et seq, and 840 et seq in FIG. 8) are optimized and this calibration function is finished (6110).

Data Processor—Flow Diagram—FIG. 14

Under the control of computer 1001, electronic processor 1070 provides analog signal data to data processor 1090. These data are correlated in the memory of computer 1001 (FIG. 8) with the position of beam 945" on nail bed 1010.

At the start (6500) of data-reduction, computer 1001 sets beam scanner 980 to an extreme corner of the scan (6510) and notes the x and y positions (FIG. 11) of beam 945". The signal level at the output of optical processor 1030 (FIG. 8) is measured (6520). The value of this signal is compared (6530) with that of a predetermined threshold. If this value is greater than the threshold value, the memory of computer 1001 records a "1" at this position (6550). If the signal value is less than the predetermined threshold value, then the same computer memory records a "0" at this position (6540). Scanner 980 then continues to scan beam 945" in raster fashion (6570, 6571, 6572, 6573) over a previously-determined portion of the area of nail 4020 (FIG. 11), taking, evaluating, and recording data at each point within this area. Data points are typically separated by 0.1 mm.

After the two-dimensional data are taken (6576), the axial direction 4040 (FIG. 11) of epidermal folds 4030 is determined by following the data maxima or minima along the x-direction 4040. Orienting the x-direction 4040 parallel to the data maxima or minima removes minor angular errors in the data. Such angular errors can occur when a subject casually places a finger under beam scanner 980 (FIG. 8) without regard to the exact orientation of the finger. Epidermal folds 4030 (FIG. 11) are now oriented along the x-axis 4040.

The data points at each y value 4050 are averaged (6575) along the x-direction 4040. This average removes minor deviations from a straight path which occur along the length of epidermal folds 4030. This average now comprises a one-dimensional data array, representative of the interfold distances $\Delta y_1, \ldots, \Delta y_n$ (FIG. 11). These data resemble information contained in a naturally-occurring "bar code" since they record spacings in a uni-dimensional scan across a number of parallel lines.

When a new subject of known identity is scanned, the data associated with this subject are saved in a database (not shown). This database is preferably stored on the hard disk of computer 1001 (FIG. 8), but it may also be stored at a distance on a "server" computer. At this point, data taking is complete (6580). These data for known subjects are called "inaugural data". Since this subject is known, the inaugural data can be updated each time the subject is identified. Updating data for each previously identified subject compensates for minor changes which occur due to injuries, aging, and the like.

When a subject of unknown identity is scanned, the data associated with this subject are saved at a new location in the memory of computer 1001. The new scan is then compared with previously saved scans in the database of known individuals, as described in connection with FIG. 15.

Pattern Recognition Algorithm—Flow Diagram—FIG. 15

After averaging in the x-direction, the above scanning procedure results in data which are saved in a one-dimensional data array (not shown) with data points being taken in the y-direction 4050 (FIG. 11). These data are binary, i.e. either a 1 if the signal level 6550 (FIG. 14) was greater than a predetermined threshold, or a 0 if the signal level 6540 was less than that threshold. These data resemble a naturally created "bar code". They are of the form Data $(y_1)$, Data $(Y_2), \ldots,$ Data $(y_n)$ The above data array can be further reduced to a series of lines and spacings of known widths. This reduced data set is of the same form, but the first number represents a datum, the second number represents the spacing between the first two lines (ONES), the third number represents the spacing between the second and third line, and so forth. Those skilled in the art of bar code applications are aware of numerous binary line-and-space data representation schemes. These schemes will faithfully represent the bar code-like data contained in the nail bed structure.

Data from the nails of previously scanned subjects are called "inaugural scans". These scans serve as a reference to identify individuals whose identity has been previously entered into the database (not shown) associated with the pattern recognition algorithm. The information from these scans is stored in the same format as the current data from the unknown subject.

At the start (7000) of the algorithm (FIG. 15), a first one-dimensional data array is filled with the current subject's nail scan data (7010). A second, one-dimensional data array is filled previously scanned, stored data for a first known subject (7020). These data are compared at each position (7030). If the data are equal at all (or most) scan positions (7040), then the algorithm is finished (7050). A positive identification has been made.

If the data are not equal (7040), then if more stored data are available for comparison (7060), the second one-dimensional array is filled with data for another subject (7070), and another comparison is done. This process continues until a positive identification is made (7050), or until it terminates with no further data and no identification (7080).

More complex and elaborate identification algorithms are possible. For example, if some, but not all, of the positions in the scanned pattern in the nailbed have matching data then identification along with a certain confidence level can be established for the identification of the pattern in the individual's nailbed.

Summary, Ramifications, and Scope

It is thus seen that the present system provides a way to unambiguously identify individuals, preferably by optically scanning their fingernail beds and analyzing their birefringent structures. Several advantages of the present invention are to provide an improved method and apparatus for rapid identification of individuals which is relatively fast and inexpensive and which is not susceptible to errors which arise from changes due to aging, hoarseness, surface injuries, and the like. The improved apparatus uses a single, less expensive light source than required in the prior art patent. Further, it provides a means for identifying individuals, which does not carry the social stigma of law enforcement, which does not require the storage or manipulation of vast amounts of data as are used in prior-art schemes, and which is neither cumbersome nor intrusive. Still further, it provides a means for identification of individuals which is computerized and can yield unambiguous results, and which automatically analyzes fingernail beds. Another advantage is the provision of a system in which the data reduces to a naturally created "barcode". A further advantage is the provision of a system which is insensitive to differences in the angular orientation of the subject's finger, relative to the apparatus. Still another advantage is the identification of individuals through analysis of the birefringent material in their nail beds.

While the foregoing explanation contains many specificities, these are given by way of example only and should not be construed as limiting. Many ramifications are possible within the scope of the invention. E.g., although the preferred embodiment has been described for use with fingernails, other body structures, such as toenails, can be analyzed with equal effectiveness. Instead of a galvanometric scanner, an acousto-optical scanner can be used. Instead of a single line scan which is detected by a single photocell, a linear or two-dimensional array of photocells can be used. These photocells can be arranged within a charge-coupled device (CCD) sensor, for example. Even a television camera electron tube can be used. More or less data representative of a person's nail bed can be saved. Instead of a binary number, the data can be saved as multi-bit, digital bytes or as analog information. Rather than using the absolute row numbers to comprise the identifying number string, a differencing method can be used. In this method, the position of the first usable data point is regarded as the datum for subsequent locations. Instead of absolute correlation of inaugural and field data, a partial match between a stored identity can be statistically analyzed. This analysis provides an identity which is qualified as to a statistical level of confidence.

In some cases, alternative components can replace the preferred components which comprise the system of FIG. 8 without adversely affecting operation of the overall system. For example, light source 810 (shown in detail in FIG. 9) can utilize a wideband light source such as an incandescent bulb. Light from the bulb passes through one or more optical filters which define its central wavelength and bandwidth. Alternatively, a light source such as a light-emitting diode (LED) with the desired central wavelength and bandwidth can be used. Yet another alternative is to use an LED with nearly optimal properties and to filter its light to obtain the required characteristics.

The relative positions of modulating frequency source 880 and frequency shifter 900 can be interchanged without adversely affecting operation of the system. The orientations of polarization of polarizers 940 and 952 can be exchanged without adversely affecting operation of the system.

Instead of a galvanometric beam scanner arrangement 980, one or more rotating prisms or holograms can equivalently be used.

While the present system employs elements which are well known to those skilled in the separate arts of optics, signal analysis and electronics, it combines elements from these fields in a novel way which produces a new result not heretofore discovered.

Accordingly the scope of this invention should be determined, not by the embodiments illustrated, but by the appended claims and their legal equivalents.

We claim:

1. A system for determining the identity of a pattern on an area, comprising:
   a. a light source other than a laser, having a predetermined spectral bandwidth for producing a collimated beam of light,
   b. a beam splitter for splitting said collimated beam of light into a plurality of beams,
   c. a modulating frequency source for modulating the frequency of one of said plurality of beams,
   d. a frequency shifter for shifting the frequency of said modulating frequency,
   e. a plurality of acousto-optic modulators for modulating the intensities of said respective plurality of beams,
   f. a plurality of crossed polarizers for polarizing said respective plurality of beams,
   g. a directional coupler for reflecting one of said beams to provide a reflected beam and redirecting said reflected beam,
   h. a beam scanner for causing one of said beams to scan across said area,
   i. an optical processor for processing the combined energies of said plurality of beams, and providing a data output,
   j. an electronic processor for processing said data output from said optical processor to provide processed data, and
   k. a data processor for processing said processed data from said electronic processor,
   l. said data processor containing a pattern recognition algorithm and previously stored data and arranged to compare said previously-stored data with said processed data from said electronic processor,
   m. said pattern recognition algorithm also arranged to provide an indication of the identity of said pattern based on its comparison of said previously-stored data with said processed data from said electronic processor.

2. The system of claim 1 wherein said light source is a light-emitting diode.

3. The system of claim 1 wherein said light source is a bandpass-filtered, incandescent lamp.

4. The system of claim 1 wherein said modulating frequency source is arranged to modulate a first of said acousto-optic modulators at a first frequency.

5. The system of claim 1 wherein said modulating frequency shifter is arranged to shift the frequency from said modulating frequency source and apply said shifted frequency to a second of said acousto-optic modulators.

6. The system of claim 1 wherein a first of said crossed polarizers is arranged to polarize light from the first of said acousto-optic modulators, and a second of said crossed polarizers is arranged to polarize light from the second of said acousto-optic modulators, the angles of polarization of said first and second polarizers being separated by ninety degrees.

7. The system of claim 1 wherein said first crossed polarizer is positioned to cause light from itself to enter said beam scanner.

8. The system of claim 1 wherein said directional coupler is positioned to cause light from itself to enter said beam scanner.

9. The system of claim 1 wherein said second crossed polarizer is positioned to cause light from itself to enter said optical processor.

10. The system of claim 1 wherein said optical processor is arranged to combine said first and second beams of light into a combined beam and detect the characteristics of said combined beam.

11. The system of claim 1 wherein said electronic processor is arranged to further refine the signal from said optical processor into amplitude and positional information.

12. The system of claim 1 wherein said data processor is arranged to utilize said analog and positional information from said electronic processor to produce a binary value of said signal corresponding to said positional information.

13. The system of claim 1 wherein said data processor is arranged to provide data to said pattern recognition algorithm and said pattern recognition algorithm is arranged to compare said data with said previously stored data for identifying an individual.

14. The system of claim 1 wherein said area is a fingernail of an individual, whereby said system can recognize the identity of said individual.

* * * * *